(12) United States Patent
Li

(10) Patent No.: US 11,435,241 B2
(45) Date of Patent: Sep. 6, 2022

(54) SMART BODY TEMPERATURE MONITORING SYSTEM

(71) Applicant: UleEco Limited, San Po Kong (HK)

(72) Inventor: Hung To Li, San Po Kong (HK)

(*) Notice: Subject to any disclaimer, the term of this patent is extended or adjusted under 35 U.S.C. 154(b) by 73 days.

(21) Appl. No.: 16/596,767

(22) Filed: Oct. 9, 2019

(65) Prior Publication Data

US 2021/0108972 A1 Apr. 15, 2021

(51) Int. Cl.

| | |
|---|---|
| *G01K 13/20* | (2021.01) |
| *G16H 40/67* | (2018.01) |
| *G16H 10/60* | (2018.01) |
| *A61B 5/00* | (2006.01) |
| *A61B 5/01* | (2006.01) |
| *A61B 5/0205* | (2006.01) |
| *A61B 5/1171* | (2016.01) |
| *G01K 1/022* | (2021.01) |
| *G01K 1/024* | (2021.01) |

(Continued)

(52) U.S. Cl.
CPC ............ *G01K 13/20* (2021.01); *A61B 5/0008* (2013.01); *A61B 5/0022* (2013.01); *A61B 5/01* (2013.01); *A61B 5/02055* (2013.01); *A61B 5/1176* (2013.01); *A61B 5/746* (2013.01); *G01K 1/022* (2013.01); *G01K 1/024* (2013.01); *G06V 20/62* (2022.01); *G06V 40/166* (2022.01); *G06V 40/172* (2022.01); *G16H 10/60* (2018.01); *G16H 40/67* (2018.01); *H04L 67/10* (2013.01); *H04W 4/12* (2013.01); *H04W 88/06* (2013.01); *A61B 5/021* (2013.01); *A61B 5/024* (2013.01)

(58) Field of Classification Search
CPC ........ G01K 13/20; G01K 1/022; G01K 1/024; G16H 40/67; G16H 10/60; A61B 5/0008; A61B 5/0022; A61B 5/01; A61B 5/02055; A61B 5/1176; A61B 5/746; A61B 5/021; A61B 5/024; G06K 9/00255; G06K 9/00288; G06K 9/325; H04L 67/10; H04W 4/12; H04W 88/06

See application file for complete search history.

(56) References Cited

U.S. PATENT DOCUMENTS

| | | | | |
|---|---|---|---|---|
| 2010/0262435 | A1* | 10/2010 | Smith ................... | G16H 10/60 705/3 |
| 2011/0228810 | A1* | 9/2011 | O'Hara .................. | G01J 5/02 374/121 |

(Continued)

OTHER PUBLICATIONS

Mansor et al, Body Temperature Measurement for Remote Health Monitoring System, 2013, IEEE, 5 pages (Year: 2013).*

(Continued)

*Primary Examiner* — John A Follansbee
*Assistant Examiner* — Raqiul A Choudhury
(74) *Attorney, Agent, or Firm* — Prakash Nama; Global IP Services, PLLC

(57) ABSTRACT

A smart body temperature monitoring system, including a thermometer that has a body temperature detection module, a CPU connected with the body temperature detection module, and a wireless communication module connected with the CPU; a cloud server having a cloud database that stores global records of one or more persons including global identification information and global body temperature data of the person; and a mobile terminal, through which the global records of the cloud database stored in the cloud server are accessed and checked.

16 Claims, 1 Drawing Sheet

(51) Int. Cl.
*H04L 67/10* (2022.01)
*H04W 4/12* (2009.01)
*H04W 88/06* (2009.01)
*G06V 20/62* (2022.01)
*G06V 40/16* (2022.01)
*A61B 5/021* (2006.01)
*A61B 5/024* (2006.01)

(56) References Cited

U.S. PATENT DOCUMENTS

| | | | | |
|---|---|---|---|---|
| 2012/0003933 | A1* | 1/2012 | Baker | A61B 5/021 455/41.2 |
| 2014/0114470 | A1* | 4/2014 | Rashid | G16H 20/13 700/235 |
| 2014/0278475 | A1* | 9/2014 | Tran | G16H 80/00 705/2 |
| 2015/0065814 | A1* | 3/2015 | Kapoor | A61B 5/14542 600/301 |
| 2016/0081559 | A1* | 3/2016 | Sofia | A61B 5/742 600/549 |
| 2016/0155310 | A1* | 6/2016 | Joao | H04W 4/021 340/573.1 |
| 2018/0064349 | A1* | 3/2018 | Kerr | A61B 5/01 |
| 2020/0349376 | A1* | 11/2020 | Raveendran | H04N 5/2258 |
| 2021/0052221 | A1* | 2/2021 | Panneer Selvam | A61B 5/486 |

OTHER PUBLICATIONS

Rusyn et al, Automated Recognition of Numeric Display Based on Deep Learning, 2019, IEEE, 4 pages (Year: 2019).*

Date added to IEEE for Rusyn et al, Automated Recognition of Numeric Display Based on Deep Learning, 2019, 2 pages (Year: 2019).*

* cited by examiner

SMART BODY TEMPERATURE MONITORING SYSTEM

BACKGROUND OF THE INVENTION

The present invention relates to the medical field, and more specifically relates to a smart body temperature monitoring system.

In some cities, kindergartens usually require parents to measure body temperatures of their kids before they go to school to ensure they do not have any fever. Specifically, at times of influenza outbreak, schools and parents have to more closely monitor the body temperatures of the kids.

Body temperatures of the kids are currently monitored as follows: parents measure the body temperatures of their kids manually, and then fill in the measured data in paper forms designed by the schools, and the kids bring the forms back to schools and hand in to the teachers. Such way of monitoring body temperatures of the kids consumes a lot of time and energy of the parents, teachers as well as the kids themselves. Specifically, if a family has many kids, or if a school has many students, data measurements, gathering and analysis would consume more time and different data may easily be mixed up.

BRIEF SUMMARY OF THE INVENTION

In view of the aforesaid disadvantages now present in the prior art, the present invention provides a smart body temperature monitoring system.

The technical solution provided by the present invention is detailed as follows:

A smart body temperature monitoring system, comprising:
- a thermometer; the thermometer comprises a body temperature detection module for capturing local body temperature data of a person identified by a local identification information, a central processing unit (CPU) connected with the body temperature detection module, and a wireless communication module connected with the CPU;
- a cloud server communicatively connected with the wireless communication module of the thermometer, comprising a cloud database; the cloud database stores global records of one or more persons, wherein a global record for each of the persons includes a global identification information and global body temperature data of the person; and
- a mobile terminal communicatively connected with the cloud server, through which the global records of the cloud database stored in the cloud server are accessed and checked.

Further, the smart thermometer also comprises a built-in storage device connected with the CPU; the built-in storage device of the thermometer is stored with a local database; the local database stores local records of one or more persons; a local record for each of the persons includes the local identification information and the local body temperature data of the person.

Further, the wireless communication module transmits the local records of the local database directly/indirectly to the cloud server and synchronizes the local records of the local database with the global records of the cloud database of the cloud server. The wireless communication module may be a Bluetooth® communication module; the Bluetooth® communication module transmits the local records of the local database to a mobile phone; the mobile phone synchronizes the local records of the local database with the global records of the cloud database of the cloud server. The wireless communication module may also be a WIFI communication module; the WIFI communication module uploads the local records of the local database directly to the cloud server via a WIFI router and synchronizes the local records of the local database with the global records of the cloud database of the cloud server. The wireless communication module may also be a mobile communication module such as a 4G or 5G communication module or proprietary wireless communication protocol directly or indirectly connected to Internet/cloud; the mobile communication module uploads the local records of the local database directly/indirectly to the cloud server via a mobile communication network and synchronizes the local records of the local database with the global records of the cloud database of the cloud server.

Further, the thermometer comprises a motion sensor connected to the CPU; the motion sensor connected to the CPU; the motion sensor controls the CPU to activate the thermometer when it is sensed that the thermometer is being triggered.

Further, the thermometer also comprises a press button module connected with the CPU for controlling the CPU to save the local body temperature data captured by the body temperature detection module to the local record of a particular person in the local database. The press button module may comprise a plurality of buttons, with each of the buttons associated with a particular person in the local database; when one of the buttons is pressed, the CPU saves the local body temperature data captured by the body temperature detection module to the local record of the corresponding person in the local database; the thermometer produces a sound alert when any of the buttons is pressed, so as to indicate which person's body temperature is currently being measured. Alternatively, the press button module may also comprise one button; each press of the button causes the CPU to save next local body temperature data captured by the body temperature detection module to the record of next person in sequence in the local database.

Further, the thermometer also comprises a camera connected with the CPU. The camera may be photographic camera, video camera or thermal imaging camera.

Further, the thermometer also comprises a face recognition module connected with the CPU; the local records of the local database further includes local face information; the face recognition module is configured to control the camera to capture face image of a person, search through the local database for a local record with its local face information matching with the captured face image so as to determine a current local record in the local database where the local body temperature data captured by the body temperature detection module is to be saved, and create a new local record if no local record of the local database has local face information matching with the captured face image and determine the new local record as the current local record.

Further, the thermometer also comprises a drug identification module connected with the CPU; the local records of the local database further include local drug information; the global records of the cloud database further include global drug information; the drug identification module is configured to control the camera to capture graphic image of a drug packaging, perform image recognition on the captured graphic image to identify drug information, and control the CPU to save the identified drug information to the current local record in the local database determined by the face recognition module.

Further, the thermometer also comprises a medical information identification module connected with the CPU; the local records of the local database further include local medical information; the global records of the cloud database further include global medical information; the medical information identification module is configured to control the camera to capture graphic image of a display screen of a medical device, perform image recognition on the captured graphic image to identify medical information, and control the CPU to save the identified medical information to the current local record in the local database determined by the face recognition module. The medical device is in the form of a blood pressure meter or heart rate meter, and the medical information is in the form of blood pressure information and heart rate information.

Further, the smart body temperature monitoring system may further comprise a second mobile terminal provided with a drug identification module to identify drug information and to transmit and store the identified drug information to a corresponding global record in the cloud database.

Further, the global records of the cloud database include a residential address and a school address, and the cloud server determines a severe fever outbreak zone based on the distribution of global body temperature data, the residential address and the school address of the global records in the cloud database and transmits corresponding alerts or messages to the mobile terminal.

The present invention has the following advantages compared with the prior art: the present invention can automatically achieve monitoring of body temperature of a person (such as a kid). When parents grab up the thermometer, the motion sensor will activate the thermometer automatically without the need of the parents to manually turn on the thermometer. Parents may then press a button that is preset by using such as a mobile application to correspond to a particular kid, to measure the kid's body temperature, and then the measured body temperature will be automatically uploaded to the cloud server with the help of for example the WIFI communication module for use by different establishments such as schools, hospitals and clinics, and a corresponding alert and message will also be automatically issued. As such, the time and energy of the parents, schools as well as the students can be saved, and the management of the students' body temperatures can be facilitated.

DETAILED DESCRIPTION OF THE INVENTION

The technical solution provided according some embodiments of the present invention will be clearly and comprehensively described below with reference to the accompanying figures. It should be noted that the embodiments as described below are only some of the many possible embodiments of the present invention and do not cover all possible embodiments. All other possible embodiments obtainable without any inventive effort by a skilled person in this field of art in accordance with the teachings of the present invention should also fall within the scope of protection of the present invention.

Figure 1:
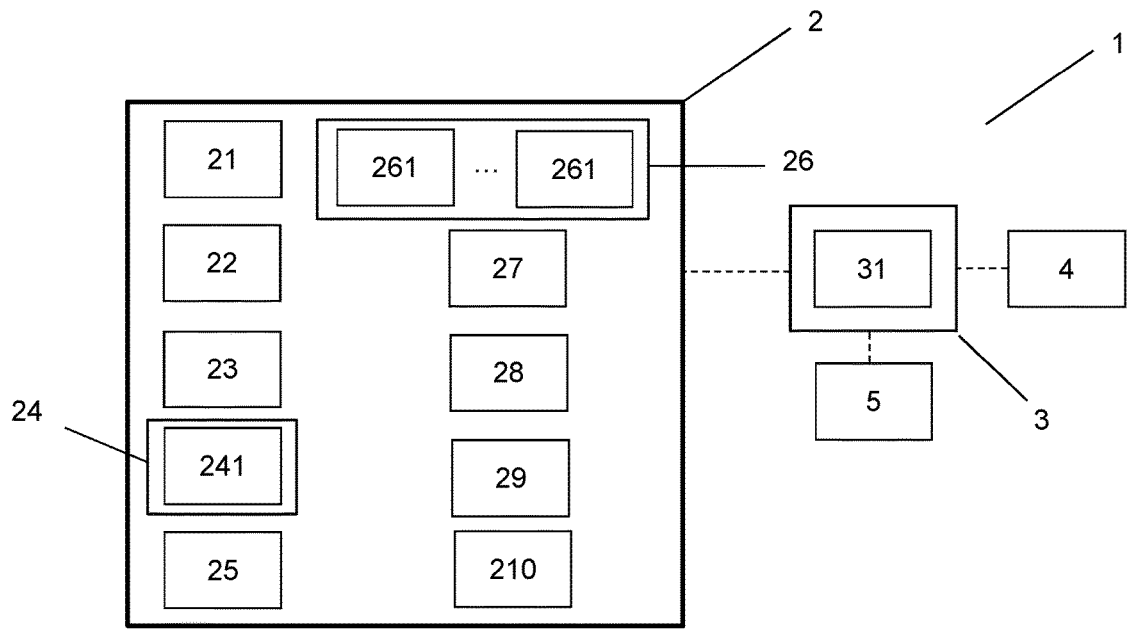
FIG. 1 is a block diagram of the present invention according to an embodiment.
Figure 2:
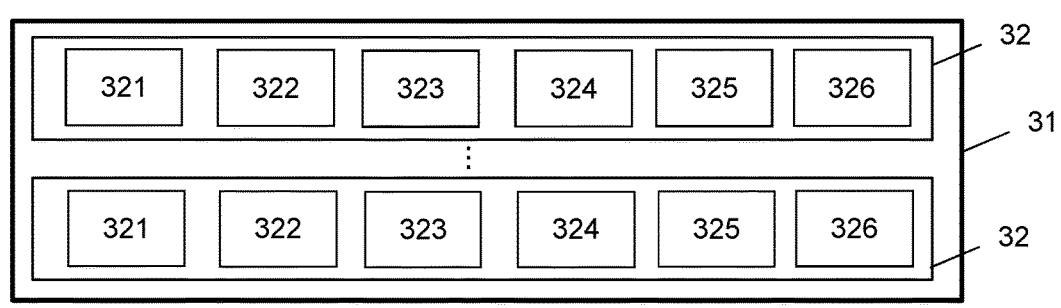
FIG. 2 shows a plurality of global records stored in the cloud database.
Figure 3:
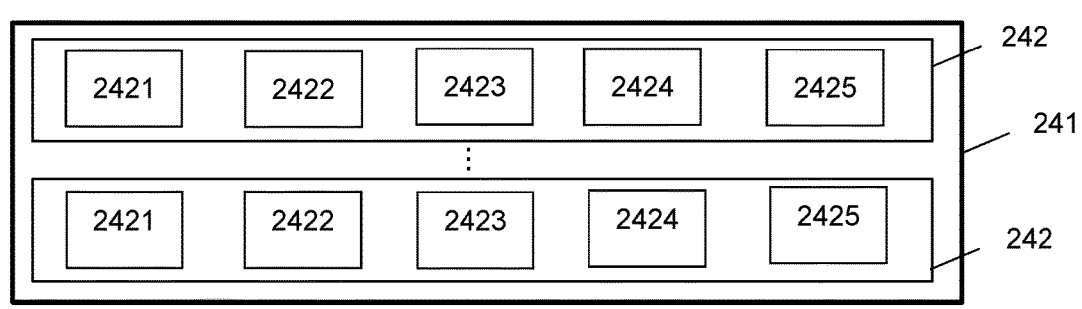
FIG. 3 shows a plurality of local records stored in the local database.

FIGS. 1 to 3 illustrate a body temperature monitoring system 1 in an embodiment of the present invention. In this embodiment, the body temperature monitoring system 1 is applied to the education sector. It comprises:

A thermometer 2; the thermometer 2 comprises a body temperature detection module 21 for capturing local body temperature data of a person (e.g. a kid) identified by a local identification information, a central processing unit (CPU) 22 connected with the body temperature detection module 21, and a wireless communication module 23 connected with the CPU 22;

A cloud server 3 communicatively connected with the wireless communication module 23 of the thermometer 2, comprising a cloud database 31; the cloud database 31 stores global records 32 of one or more persons, wherein a global record 32 for each of the persons includes a global identification information 321 and global body temperature data 322 of the person; and A mobile terminal 4 communicatively connected with the cloud server 3, through which the global records 32 of the cloud database 31 stored in the cloud server 3 are accessed and checked.

In this embodiment, the thermometer 2 also comprises a built-in storage device 24 connected with the CPU 22; the built-in storage device 24 of the thermometer 2 is stored with a local database 241; the local database stores local records 242 of one or more persons; a local record 242 for each of the persons includes the local identification information 2421 and the local body temperature data 2422 of the person.

The wireless communication module 23 transmits the local records 242 of the local database 241 directly/indirectly to the cloud server 3 and synchronizes the local records 242 of the local database 241 with the global records 32 of the cloud database 31 of the cloud server 3. The wireless communication module 23 may be a Bluetooth® communication module, a WIFI communication module and/or a mobile communication module such as a 4G or 5G cellular communication module. The Bluetooth® communication module transmits the local records 242 of the local database 241 to a mobile phone (e.g. a parent's mobile phone); the mobile phone synchronizes the local records 242 of the local database 241 with the global records 32 of the cloud database 31 of the cloud server 3. The WIFI communication module uploads the local records 242 of the local database 241 directly to the cloud server 3 via a WIFI router and synchronizes the local records 242 of the local database 241 with the global records 32 of the cloud database 31 of the cloud server 3. The mobile communication module uploads the local records 242 of the local database 241 directly/indirectly to the cloud server 3 via a mobile communication network and synchronizes the local records 242 of the local database 241 with the global records 32 of the cloud database 31 of the cloud server 3, without requiring the parent's mobile phone to be turned on.

The thermometer 2 comprises a motion sensor 25 connected to the CPU 22; the motion sensor 25 controls the CPU 22 to activate the thermometer 2 when it is sensed that the thermometer 2 is being triggered. For example, when the motion sensor 25 senses a lift of the thermometer 2, the thermometer 2 will be activated automatically. In this way, the user will feel convincement in operation even if the thermometer 2 dims or sleeps after it doesn't sense any user activity. The power of the thermometer 2 could be saved since no power is wasted in power on mode without user activity.

The thermometer 2 also comprises a press button module 26 connected with the CPU 22 for controlling the CPU 22 to save the local body temperature data captured by the body temperature detection module 21 to the local record 242 of a particular person in the local database 241. In this embodiment, the press button module 26 comprises a plurality of buttons 261, with each of the buttons 261 associated with a particular person in the local database 242 (for example, a first button is designated to associate with a first kid, and a second button is designated to associate with a second kid); when one of the buttons 261 is pressed, the CPU 22 saves the local body temperature data captured by the body temperature detection module 21 to the local record 242 of the corresponding person in the local database 241. The thermometer 2 produces different sound alert when any of the buttons 261 is pressed, so as to indicate which person's body temperature is currently being measured. In other embodiments, the press button module may comprise one button; each press of the button causes the CPU to save next local body temperature data captured by the body temperature detection module to the record of next person in sequence in the local database. The different sound alert can be applied to this embodiment too.

In this embodiment, the thermometer 2 also comprises a camera 27 connected with the CPU 22. The camera 27 may be photographic camera, video camera or thermal imaging camera. The thermometer 2 further comprises a face recognition module 28 connected with the CPU 22; the local records 242 of the local database 241 further includes local face information 2423; the face recognition module 28 is configured to control the camera 27 to capture face image of a person, search through the local database 241 for a local record 242 with its local face information 2423 matching with the captured face image so as to determine a current local record in the local database 241 where the local body temperature data captured by the body temperature detection module 21 is to be saved, and create a new local record if no local record of the local database 241 has local face information matching with the captured face image and determine the new local record as the current local record. The captured face image in photographic camera or video camera is a visible color image while the captured face image in thermal imaging camera is a heat zone image based on the thermal distribution of the face. Although the heat zone image is different from visible color image, the facial features are also recognized and are compared to the local face information in order to perform the matching. To enable this function, presetting is required during initial stage of use (for example, take a photograph of a person by using the camera, and save the photograph as the local face information 2423 of the local record 242 of that person). After presetting, the thermometer 2 can be used to measure body temperature of different persons. Instead of pressing a button, just point the camera to a person and the face recognition module 28 will automatically identify the person and determine a current local record, and the thermometer 2 can automatically store the local body temperature measured to the current local record in the local database 241

The thermometer 2 further comprises a drug identification module 29 connected with the CPU 22; the local records 242 of the local database 241 further include local drug information 2424; the global records 32 of the cloud database 31 further include global drug information 323; the drug identification module 29 is configured to control the camera 27 to capture graphic image of a drug packaging or drug itself, perform image recognition (for example by graphic to text recognition or by scanning bar code or QR code or by shape, size and color of drug to lookup a drug information database etc.) on the captured graphic image to identify drug information, and control the CPU 22 to save the identified drug information to the current local record in the local database 241 determined by the face recognition module 28.

The thermometer 2 further comprises a medical information identification module 210 connected with the CPU 22; the local records 242 of the local database 241 further include local medical information 2425; the global records 32 of the cloud database 31 further include global medical information 324; the medical information identification module 210 is configured to control the camera 27 to capture graphic image of a display screen of a medical device such as a blood pressure meter or a heart rate meter, perform image recognition on the captured graphic image to identify medical information such as blood pressure information or heart rate information, and control the CPU 22 to save the identified medical information to the current local record in the local database 241 determined by the face recognition module 28.

The body temperature monitoring system 1 further comprises a second mobile terminal 5 (e.g. a parent's mobile phone) provided with drug identification module to identify drug information and to transmit and store the identified drug information to the corresponding global record 32 in the cloud database 31. By using a mobile application, a camera of the second mobile terminal 5 can take a photo of a drug and the information of the drug can be automatically identified (e.g. by graphic/image recognition or by scanning a bar code or QR code etc.) and stored in the cloud database 31. The mobile application or otherwise the thermometer 2 can remind a sick student to take medicine or remind their parents, caretakers or any third party to administer medicine to them according to the local drug information 2424 stored in the local database 241 of the built-in storage device 24 of the thermometer 2 or the global drug information 323 stored in the cloud database 31.

The cloud server 3 may comprise a time management module; the time management module retains history of some information such as the global body temperature data 322 of each of the global records 32. These information history are very useful to a doctor. It is not necessary to worry if a person caught a fever and his body temperature fell due to medication and then rose only slightly again. However, special attention is required if a person caught a fever and his body temperature fell due to medication but then rose again to the same or even higher level than the body temperature measured when he initially caught the fever, because the person may be infected with a more serious disease. Therefore, these information history are very important.

The global records 32 of the cloud database 31 may also include residential address 325 and school address 326. The cloud server 3 can determine a severe fever outbreak zone based on the global body temperature data 322, residential address 325 and school address 326 of the global records 32 in the cloud database 31, and then reminds parents and students through mobile applications to avoid the severe fever outbreak zone so as not be get infected. Government authorities may also utilize the present invention to remind other citizens.

In some embodiments of the present invention, the cloud server 3 is also connected with for example the servers of hospitals, clinics or government body, or the mobile terminals of doctors and nurses. Applications are installed in the mobile terminals to automatically obtain updated push notifications about the body temperatures of the students so that hospitals, clinics or government body are timely informed of the body temperature information of the students and thus timely prepared for corresponding medical treatments. Doctors from different areas may directly access the medical records such as fever and medication history via the present invention, and it is particularly useful during emergency situation.

The preferred embodiments of the present invention are described above. It should be noted that improvements and modifications without deviating from the principle of the present invention may be possibly achieved by a person skilled in this field of art, and should fall within the scope of protection of the present invention.

What is claimed is:

1. A smart body temperature monitoring system, comprising:
    a thermometer; the thermometer comprises a body temperature detection module for capturing local body temperature data of a person identified by a local identification information, a central processing unit (CPU) connected with the body temperature detection module, and a wireless communication module connected with the CPU;
    a cloud server communicatively connected with the wireless communication module of the thermometer, comprising a cloud database; the cloud database stores global records of one or more persons, wherein a global record for each of the persons includes a global identification information and global body temperature data of the person; and
    a mobile terminal communicatively connected with the cloud server, through which the global records of the cloud database stored in the cloud server are accessed and checked;
    the thermometer also comprises a built-in storage device connected with the CPU; the built-in storage device of the thermometer is stored with a local database; the local database stores local records of one or more persons; a local record for each of the persons includes the local identification information and the local body temperature data of the person;
    the wireless communication module transmits the local records of the local database directly/indirectly to the cloud server and synchronizes the local records of the local database with the global records of the cloud database of the cloud server;
    the thermometer also comprises a camera connected with the CPU
    the thermometer further comprises a face recognition module connected with the CPU; the local records of the local database further includes local face information: the face recognition module is configured to control the camera to capture face image of a person, search through the local database for a local record with its local face information matching with the captured face image so as to determine a current local record in the local database where the local body temperature data captured by the body temperature detection module is to be saved, and create a new local record if no local record of the local database has local face information matching with the captured face image and determine the new local record as the current local record.

2. The smart body temperature monitoring system of claim 1, wherein the wireless communication module transmits the local records of the local database to a mobile phone; the mobile phone synchronizes the local records of the local database with the global records of the cloud database of the cloud server.

3. The smart body temperature monitoring system of claim 1, wherein the wireless communication module is a WIFI communication module; the WIFI communication module uploads the local records of the local database directly to the cloud server via a WIFI router and synchronizes the local records of the local database with the global records of the cloud database of the cloud server.

4. The smart body temperature monitoring system of claim 1, wherein the wireless communication module is a mobile communication module; the mobile communication module uploads the local records of the local database directly/indirectly to the cloud server via a mobile communication network and synchronizes the local records of the local database with the global records of the cloud database of the cloud server.

5. The smart body temperature monitoring system of claim 1, wherein the thermometer comprises a motion sensor connected to the CPU; the motion sensor controls the CPU to activate the thermometer when it is sensed that the thermometer is being triggered.

6. The smart body temperature monitoring system of claim 1, wherein the thermometer also comprises a press button module connected with the CPU for controlling the CPU to save the local body temperature data captured by the body temperature detection module to the local record of a particular person in the local database.

7. The smart body temperature monitoring system of claim 6, wherein the press button module comprises a plurality of buttons, with each of the buttons associated with a particular person in the local database; when one of the buttons is pressed, the CPU saves the local body temperature data captured by the body temperature detection module to the local record of the corresponding person in the local database.

8. The smart body temperature monitoring system of claim 7, wherein the thermometer produces a sound alert when any of the buttons is pressed, so as to indicate which person's body temperature is currently being measured.

9. The smart body temperature monitoring system of claim 6, wherein the press button module comprises one button; each press of the button causes the CPU to save next local body temperature data captured by the body temperature detection module to the record of next person in sequence in the local database.

10. The smart body temperature monitoring system of claim 1, wherein the camera is photographic camera, video camera or thermal imaging camera.

11. The smart body temperature monitoring system of claim 1, wherein the thermometer further comprises a drug identification module connected with the CPU; the local records of the local database further include local drug information; the global records of the cloud database further include global drug information; the drug identification module is configured to control the camera to capture graphic image of a drug packaging or drug itself, perform image recognition on the captured graphic image to identify drug information, and control the CPU to save the identified drug information to the current local record in the local database determined by the face recognition module.

12. The smart body temperature monitoring system of claim 1, wherein the thermometer further comprises a medical information identification module connected with the CPU; the local records of the local database further include local medical information; the global records of the cloud database further include global medical information; the medical information identification module is configured to control the camera to capture graphic image of a display screen of a medical device, perform image recognition on the captured graphic image to identify medical information, and control the CPU to save the identified medical information to the current local record in the local database determined by the face recognition module.

13. The smart body temperature monitoring system of claim 12, wherein the medical device is in the form of a blood pressure meter or heart rate meter, and the medical information is in the form of blood pressure information and heart rate information.

14. The smart body temperature monitoring system of claim 1 further comprising a second mobile terminal; the global records of the cloud database further includes global drug information; the second mobile terminal is provided with a drug identification module to identify drug information and to transmit and store the identified drug information to a corresponding global record in the cloud database.

15. The smart body temperature monitoring system of claim 1, further comprising a second mobile terminal; the global records of the cloud database further includes global medical information; the second mobile terminal is provided with a medical information identification module to identify medical information and to transmit and store the identified medical information to a corresponding global record in the cloud database.

16. The smart body temperature monitoring system of claim 1, wherein the global records of the cloud database include a residential address and a school address, and the cloud server determines a fever outbreak zone based on distribution of the global body temperature data, the residential address and the school address of the global records in the cloud database and transmits corresponding alerts or messages to the mobile terminal, an external control system or institutional alerting system for a relevant authority to take school-wise, city-wise or country-wise action in response to the outbreak.

* * * * *